(12) United States Patent
De Santis

(10) Patent No.: US 7,883,889 B2
(45) Date of Patent: Feb. 8, 2011

(54) ANTIGEN PRESENTING CELLS, METHOD FOR THEIR PREPARATION AND THEIR USE FOR CANCER VACCINES

(75) Inventor: Rita De Santis, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 970 days.

(21) Appl. No.: 10/485,351

(22) PCT Filed: Jul. 25, 2002

(86) PCT No.: PCT/IT02/00488

§ 371 (c)(1), (2), (4) Date: Jan. 30, 2004

(87) PCT Pub. No.: WO03/012086

PCT Pub. Date: Feb. 13, 2003

(65) Prior Publication Data

US 2004/0185563 A1 Sep. 23, 2004

(30) Foreign Application Priority Data

Jul. 30, 2001 (WO) ........................ PCT/IT01/00419

(51) Int. Cl.
*A61K 39/00* (2006.01)
*C12N 5/07* (2010.01)
(52) U.S. Cl. .................... 435/325; 424/93.21
(58) Field of Classification Search ................. 435/325; 424/93.21
See application file for complete search history.

(56) References Cited

U.S. PATENT DOCUMENTS

| | | | |
|---|---|---|---|
| 6,613,753 | B2 | 9/2003 | Rubinfeld |
| 2003/0119187 | A1 | 6/2003 | De Santis |
| 2004/0185563 | A1 | 9/2004 | De Santis |
| 2005/0002920 | A1 | 1/2005 | De Santis |

FOREIGN PATENT DOCUMENTS

| | | |
|---|---|---|
| WO | 03/012085 | 2/2003 |
| WO | 03/012086 | 2/2003 |

OTHER PUBLICATIONS

Danbara M et al. Molecular Immunology 38: 1161-1166, 2001.*
Stedman's Medical Dictionary 27th Edition (definition of "vaccine" (pp.1-5)).*
Moigeon, Vaccine, 19: 1305-1326 (2001).*
Kirkin et al. Cancer Investigation, 20 (2): 222-236 (2002)).*
Bodey et al. (Anticancer Res. 20:2665-76 (2000)).*
Radoja et al. (Mol Med 6:465-79 (2000)).*
Shickijo et al. (Japanese J. Can. Res. 87:751-756 (1996)).*
Hu et al. (Endocrinology, 141, No. 12: 4428-4435 (2000)).*
Spisek et al. (Cancer Immunol. Immunther. 50:417-427 (2001)).*
Crammer et al. (Cancer Immunol. Immunther. 53:275-306 (2004)).*
Osada et al. (Inter. Rev. Immunol. 25(5/6):377-413 (2006)).*
Garderet et al. (J. Hematherap. & Stem cell res. 10:553-567 (2001)).*
Thurner et al. (J. Immunol. Methods 223:1-15 (1999)).*
Bartolomei et al. "Genomic imprinting in mammals" Annu. Rev. Genet. 31:493-525, abstract only (1997).
Dunnion et al. "Human antigen-presenting cell/tumour cell hybrids stimulate strong allogeneic responses and present tumour-associated antigens to cytotoxic T cells in vitro" Immunol. 98:541-550 (1999).
Mackensen et al. "Phase I study in melanoma patients of a vaccine with peptide-pulsed dendritic cells generated in vitro from CD34 hematopoietic progenitor cells" Int. J. Cancer 86:385-392 (2000).
Weber et al. "Expression of the MAGE-1 tumor antigen is up-regulated by the demethylating agent 5-aza-2'-deoxycytidine" Cancer Res. 54:1766-1771 (1994).
Bartolomei et al. "Genomic imprinting in mammals" Annu. Rev. Genet. 31:493-525 (1997).
Coral et al. "Prolonged upregulation of the expression of HLA class I antigens and costimulatory molecules on melanoma cells treated with 5-aza-2'-deoxycylidine (5-aza-CdR)" J. Immunotherap. 22:16-24 (Jan. 1999).
McKearn et al. "B cell subsets and differential responses to mitogens" Immunol. Rev. 64:5-23 (1982).
Meidenbauer et al. "Dendritic cells for specific cancer immunotherapy" Biol. Chem. 382:507-520 (Apr. 2001).
Moldenhauer et al. "Use of a histone deacetylase inhibitor to optimize the induction of a leukemia-specific cytotoxic T-cell response by dendritic cells derived from AML blasts" Blood 96:118a, abstract 508 (Nov. 2000).
Nickoloff & Turka "Immunological functions of non-professional antigen-presenting cells: New insights from studies of T-cell interactions with keratinocytes" Immunol. Today 15:464-469 (Oct. 1994).
Pedone et al. "Role of histone acetylation and DNA methylation in the maintenance of the imprinted expression of the *H19* and *Igf2* genes" FEBS Lett. 458:45-50 (1999).
Roddie & Turner "Leukemic blasts from patients with karyotypically poor risk AML are resistant to cytokine induced differentiation into dendritic like cells" Blood 96:707a, abstract 3053 (Nov. 2000).
dos Santos et al. "Heterogeneous expression of the SSX cancer/testis antigens in human melanoma lesions and cell lines" Cancer Res. 60:1654-1662 (Mar. 2000).

(Continued)

*Primary Examiner*—Lynn Bristol
(74) *Attorney, Agent, or Firm*—Lucas & Mercanti, LLP

(57) ABSTRACT

The present invention discloses a method of generation of antigen presenting cells, comprising: a collecting said cells from a subject, b. activating said collected cells; c. culturing and optionally expanding ex vivo said activated cells; d. treating said cultured and optionally expanded cells with DNA hypomethylating agents so that said cells concomitantly express multiple tumor associated antigens. The cells obtainable according to the method of the present invention, as well as the cellular components thereof whether alone or in combination with said cells, are useful for prevention and treatment of malignancies of different histotype that constitutively express one or more of the multiple tumor associated antigens that are expressed in said cells. Conveniently, said cells and/or cellular components are in the form of a vaccine. Said vaccines are advantageous over the prior art in that as they concomitantly express multiple/all methylation-regulated tumor associated antigens.

12 Claims, 6 Drawing Sheets

OTHER PUBLICATIONS

Sauerwein et al. "Induction of immunoglobulin M production by pokeweed mitogen and interleukin-2: Different responses by human peripheral blood cells and tonsil cells" Clin. Immunol. Immunopathol. 39:431-441 (Jun. 1986).

Schultze et al. "CD40-activated human B cells: An alternative source of highly efficient antigen presenting cells to generate autologous antigen specific T cells for adoptive immunotherapy" J. Clin. Invest. 100:2757-2765 (Dec. 1997).

International Search Report for PCT/IT2002/000488, five pages, dated Oct. 7, 2002.

Int'l Preliminary Examination Report for PCT/IT2002/000488, eight pages, dated Oct. 17, 2003.

James, S., Measurement of Basic Immunological Characteristics of Human Mononuclear Cells, Current Protocols in Immunology, Section II, Unit 7.10, 1994.

Enomoto, M. et al., "In vitro generation of dendritic cells derived from cryopreserved CD34+ cells mobilized into peripheral blood in lymphoma patients" Cytotherapy, 2000; 2(2): 95-104.

Tuting, T., "The immunology of cutaneous DNA immunization" Curr Opin Mol Ther, Apr. 1999; 1(2): 216-25.

Li, J. et al., "Expression of BAGE, GAGE, and MAGE Genes in Human Gastric Carcinoma" Clinical Cancer Research, vol. 2, 1619-1625, Sep. 1996.

Holliday, R., "Strong Effects of 5-Azacytidine on the In Vitro Lifespan of Human Diploid Fibroblasts" Exp. Cell Res., vol. 166, pp. 543-552, 1986.

Weiser, T., "Sequential 5-Aza-2'-deoxycytidine-Depsipeptide FR901228 Treatment Induces Apoptosis Preferentially in Cancer Cells and Facilitates Their Recognition by Cytolytic T-Lymphocytes Specific for NY-ESO-1" J. Immunotherapy, vol. 24, No. 2, pp. 151-161, 2001.

* cited by examiner

Figure 1. Proliferation of autologous (aMLR) PBMC (R) stimulated with ADHAPI-Cells/B-EBV (□) or control (◆) B-EBV cells (S)[a]
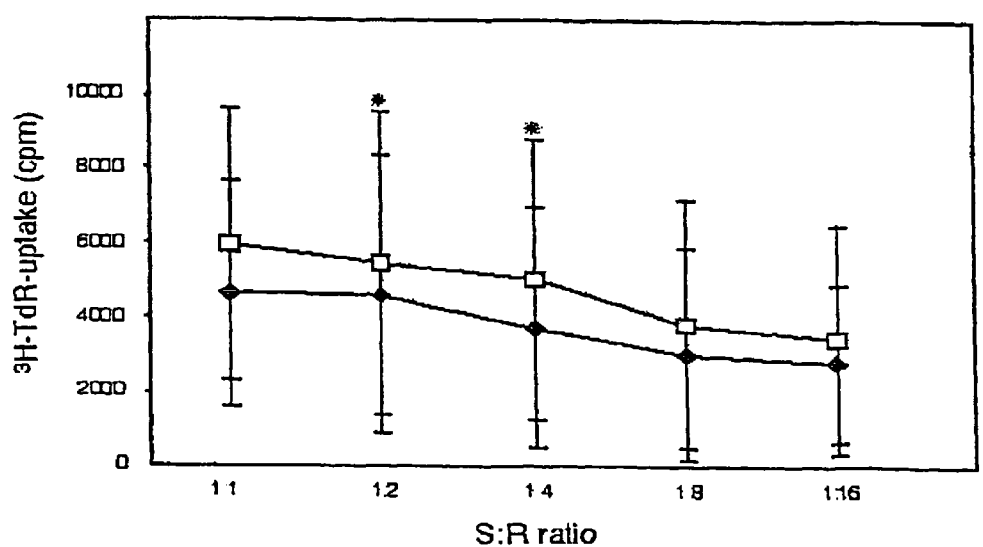
[a]Data represent the mean values (cpm)±SD of [3H]-TdR uptake obtained in four independent experiments.

Figure 2. Proliferation of autologous (aMLR) PBMC (R) stimulated with ADHAPI-Cells/PWM-B (□) or control (♦) PWM-B cells (S)[a]
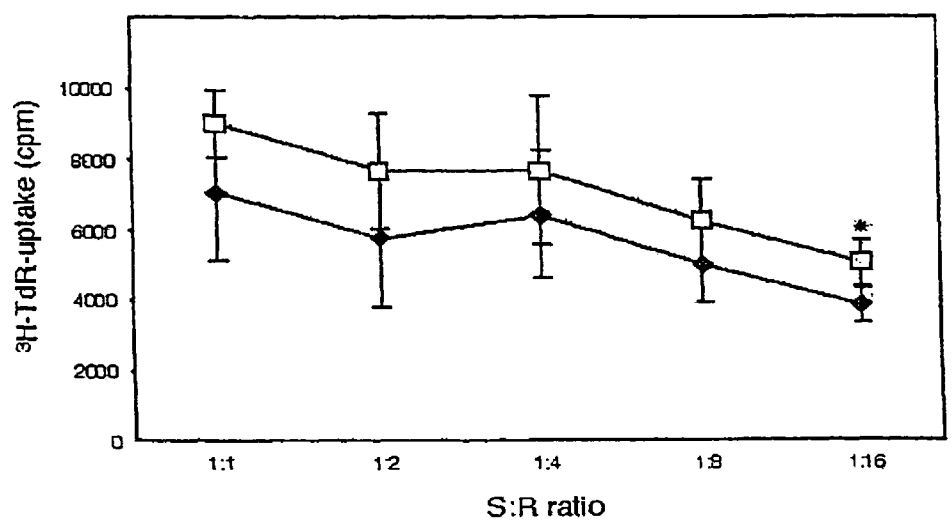
[a] Data represent the mean values (cpm)±SD of [3H]-TdR uptake obtained in four independent experiments.

Figure 3. Proliferation of autologous (aMLR) PBMC (R) stimulated with ADHAPI-Cells/CD40L-B (□) or control (♦) CD40L-B cells (S)[a]
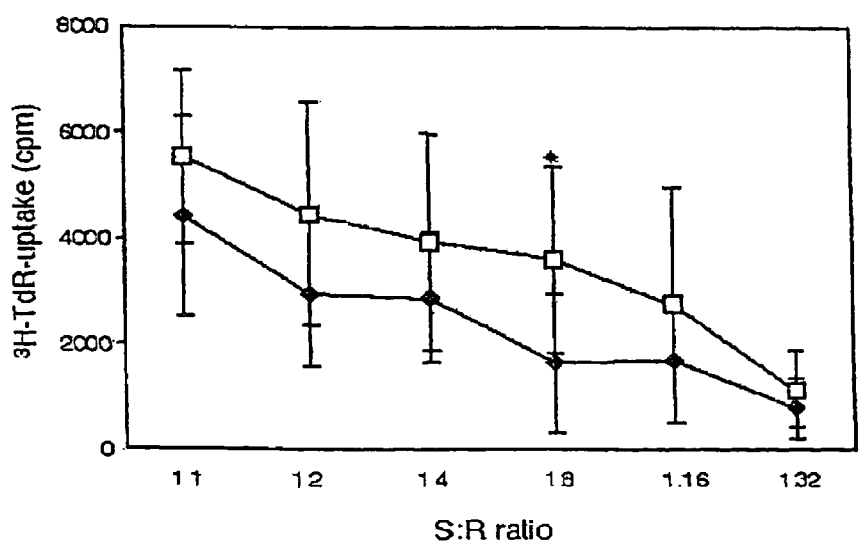
[a]Data represent the mean values (cpm)±SD of [3H]-TdR uptake obtained in eight independent experiments Figure 4. Proliferation of allogeneic (MLR) and autologous (aMLR) PBMC (R) stimulated with ADHAPI-Cells/PWM-PBMC (□) or control (◆) PWM-PBMC cells (S)[a]
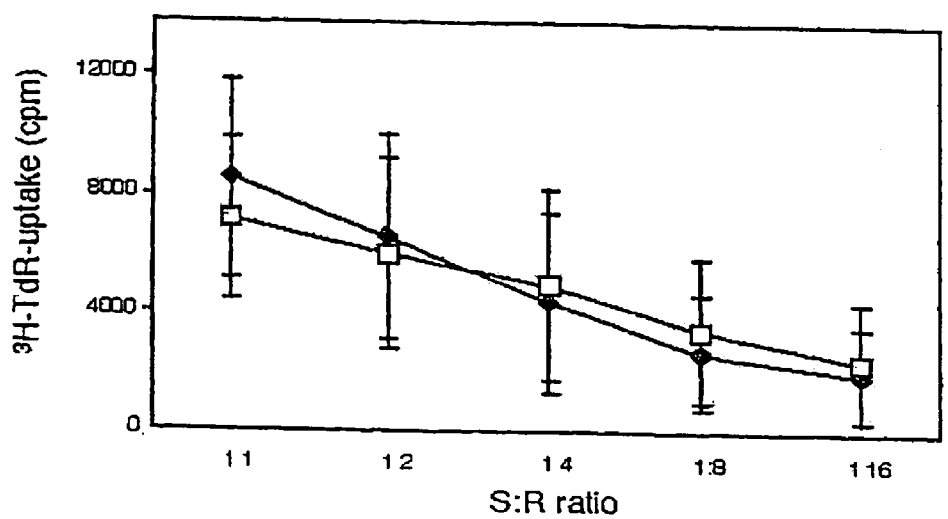
[a]Data represent the mean values (cpm)±SD of [3H]-TdR uptake obtained in four independent experiments.

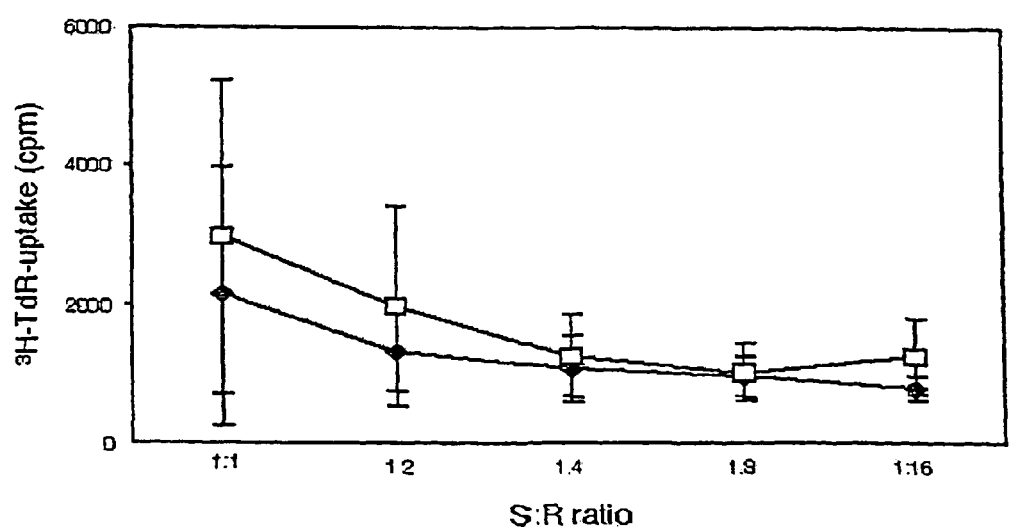
Figure 5. Proliferation of autologous (aMLR) PBMC (R) stimulated with ADHAPI-Cells/PHA-PBMC (□) and control (♦) PHA-PBMC
*Data represent the mean values (cpm)±SD of [3H]-TdR uptake obtained in five independent experiments.

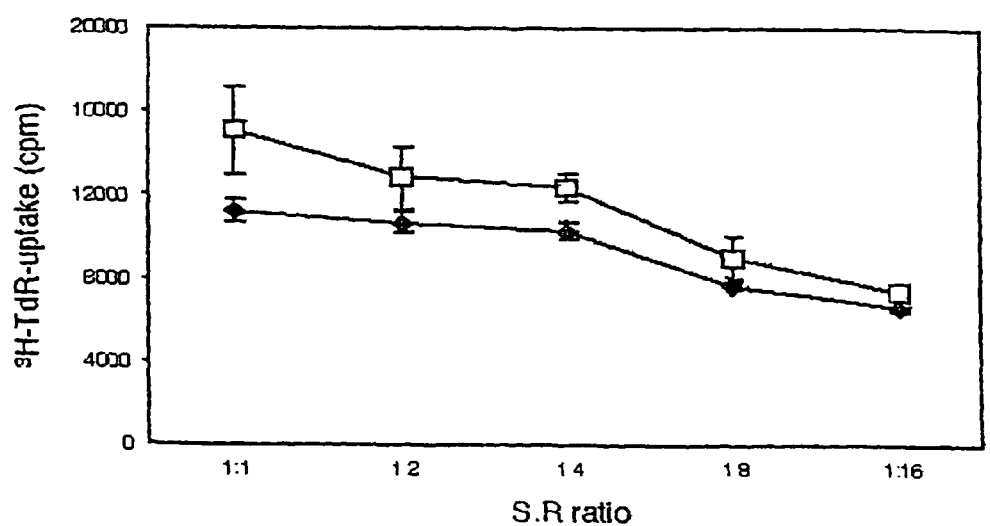
Figure 6. Proliferation of autologous (aMLR) PBMC (R) stimulated with ADHAPI-Cells/PHA+PWM-PBMC (□) or control (♦) PHA+PWM-PBMC (S)[a]
[a]Data represent the mean values (cpm)±SD of [3H]-TdR uptake obtained in four independent experiments.

ANTIGEN PRESENTING CELLS, METHOD FOR THEIR PREPARATION AND THEIR USE FOR CANCER VACCINES

This application is the U.S. national phase of international application PCT/IT02/00488 filed Jul. 25, 2002 which designated the U.S., and which in turn claims the benefit and priority of PCT/IT01/00419 filed Jul. 30, 2001, the entire contents of both are hereby incorporated by reference.

The present invention relates to the medical field, in particular to products, substances and compositions for use in methods for the treatment of human or animal subjects, more in particular for the diagnosis, treatment, and prevention of cancer. The present invention relates to cancer vaccines and methods for their preparation.

BACKGROUND OF THE INVENTION

Several tumor-associated antigens (TAA) constitutively expressed by transformed cells of different histotype have been recently identified (Renkvist N. et al. *Cancer Immunol. Immunother.* 50:3-15,2001).

A number of these TAA can provide multiple immunodominant antigenic peptides recognized by CD8+ cytotoxic T lymphocytes (CTL) in the context of specific HLA class I allospecificities (Renkvist N. et al. *Cancer Immunol. Immunother.* 50:3-15,2001); furthermore selected TAA, such as for example MAGE (Jager E. et al., *J. Exp. Med.,* 187: 265-270, 1998), NY-ESO-1 (Jager E. et al., *J. Exp. Med.,* 187: 265-270, 1998), SSX (Tureci O, et al. *Cancer Res;* 56(20):4766-72 1996), tyrosinase (Topalian S. L. et al., *J. Exp. Med.,* 183: 1965-1971, 1996.), Melan-A/MART-1 (Zarour H. M. et al., *Proc. Natl. Acad. Sci. USA,* 97: 400-405, 2000) concomitantly include epitopes recognized by CD4+ T lymphocytes in the context of specific HLA class II allospecificities, thus being able to induce a TAA-directed humoral immune response (Wang R. F., *Trends Immunol.,* 22: 269-276, 2001).

Different classes of TAA that may play a major role as therapeutic targets have been identified:
  i) cancer-testis antigens (CTA), expressed in tumors of various histology but not in normal tissues, other than testis and placenta such as for example MAGE, GAGE, SSX SART-1, BAGE, NY-ESO-1, XAGE-1, TRAG-3 and SAGE, some of which represent multiple families (Traversari C., *Minerva Biotech.,* 11: 243-253, 1999);
  ii) differentiation-specific antigens, expressed in normal and neoplastic melanocytes, such as for example tyrosinase, Melan-A/MART-1, gp100/Pmel17, TRP-1/gp75, TRP-2 (Traversari C., *Minerva Biotech,* 11: 243-253, 1999);
  iii) antigens over-expressed in malignant tissues of different histology but also present in their benign counterpart, for example PRAME (Ikeda H. et al., *Immunity,* 6: 199-208, 1997), HER-2/neu (Traversari C., *Minerva Biotech,* 11: 243-253, 1999), CEA, MUC-1(Monges G. M. et al., *Am. J. Clin. Pathol.,* 112: 635-640, 1999), alpha-fetoprotein (Meng W. S. et al., *Mol. Immunol.,* 37. 943-950, 2001);
  iv) antigens derived from point mutations of genes encoding ubiquitously expressed proteins, such as MUM- 1, β-catenin, HLA-A2, CDK4, and caspase 8 (Traversari C., *Minerva Biotech.,* 11:243-253, 1999);
  v) viral antigens (Traversari C., *Minerva Biotech.,* 11: 243-253, 1999).

In addition to TAA, the cellular elements that are crucial for their effective immunogenicity and efficient recognition by host's T lymphocytes include HLA class I and HLA class II antigens, and co-stimulatory/accessory molecules (e.g., CD40, CD54, CD58, CD80, CD81) (Fleuren G. J. et al., *Immunol. Rev.,* 145: 91-122, 1995).

Among known classes of TAA, CTA are particularly suitable therapeutic targets for active specific immunotherapy of cancer patients, because of their limited expression in normal tissues and their known in vivo immunogenicity in living subjects, in particular mammals, humans included (Jager E. et al., *J. Exp. Med.,* 187: 265-270, 1998; Rejnolds S. R. et al., *Int. J. Cancer,* 72: 972-976, 1997). However, the heterogeneous expression of specific CTA among neoplastic lesions of different patients limits their biological eligibility to CTA-directed therapeutic vaccination. In fact, malignant lesions of distinct cancer patients can frequently express only selected CTA (Sahin U. et al., *Clin. Cancer Res.,* 6: 3916-3922, 2000), additionally down-regulated (Lethž B. et al., *Melanoma Res.,* 7: S83-S88, 1997) and/or heterogeneous (dos Santos N. R. et al., *Cancer Res.,* 60: 1654-1662, 2000) expression of specific CTA within individual neoplastic lesions has also been reported (Jungbluth A. A. et al., *Br. J. Cancer,* 83: 493-497, 2000). These events, that can occur in vivo separately or concomitantly, may also contribute to the constitutively poor immunogenicity of malignant cells favouring disease progression (Speiser D. E. et al., *J. Exp. Med.,* 186: 645-653, 1997), and may as well lead to in vivo immunoselection of neoplastic cells with the emergence of CTA-negative clones, in the course of immunologic treatment against specific CTA. Thus, immunotherapeutic approaches that focus on the immunologic targeting of distinct immunogenic epitopes of single CTA cannot be applied to large numbers of cancer patients, due to the absence or the possibly down-regulated expression of target CTA in their neoplastic lesions; furthermore, the immunological targeting of single CTA in vivo may generate CTA-loss tumor variants that efficiently escape treatment-induced/amplified CTA-specific immune response. An additional limit to therapeutic approaches that target single CTA derive from their heterogeneous intralesional expression (Schultz-Thater E. et al., *Br. J. Cancer,* 83: 204-208, 2000), moreover, the presentation of distinct immunogenic epitopes of single CTA by specific HLA class I or HLA class II allospecificities allows treatment only of patients with certain defined HLA phenotypes.

To partially obviate to these limitations, recent therapeutic strategies are utilizing more than one immunogenic epitope of single or multiple CTA, or the whole CTA protein as vaccinating agent (*Conference on Cancer Vaccines,* Eds. Ferrantini M. and Belardelli F., Rome-Italy, Nov. 15-16, 1999; http://www.cancerresearch.org).

Accordingly, there is a strongly felt need for a cancer vaccine which can overcome the drawbacks of the state of the art, in particular poor immunogenicity, in vivo immunoselection, the possibility to practice a cancer vaccine on a wide population of cancer patients, not limited to the specific single targeted CTA, or TAA, and in that the cancer vaccine not be "restricted" to selected HLA class I and/or HLA class II antigens.

Recent in vitro evidences have demonstrated that the expression of all CTA genes that have been investigated, among the so far known, is induced or up-regulated in neoplastic cells of different histology following their exposure to DNA hypomethylating agents (dos Santos N. R. et al., *Cancer Res.,* 60: 1654-1662, 2000; Weber J. et al., *Cancer Res.,* 54: 1766-1771, 1994) CTA induction was found to be persistent being still detectable several weeks after the end of treatment. These findings support the notion that CTA belong to a class of TAA that is comprehensively regulated by DNA methylation. Furthermore, treatment of neoplastic cells with DNA hypomethylating agents induced a concomitant and persistent up-regulation of their expression of HLA class I antigens and of investigated HLA class I allospecificities, and also up-modulated the expression of the co-stimulatory/accessory molecules CD54 and CD58 (Coral S. et al., *J. Immunother.*, 22: 16-24, 1999).

Notwithstanding their promising therapeutic profile, CTA, however, show a number of drawbacks, such as that specific CTA so far investigated show a heterogeneous expression within distinct neoplastic lesions, with the co-existence of CTA-positive and -negative malignant cells; that only selected CTA among the ones so far identified may be expressed on distinct neoplastic lesions, independently from their hystological origin; that threshold levels of expression of specific CTA on neoplastic cells are required for their recognition by CTA-specific CTL and that vaccination against a specific CTA requires an appropriate HLA class I and, for selected CTA also HLA class II phenotype of patients.

Due to their unique biologic features, selected CTA are being utilized in different clinical trials that aim to induce or potentiate a CTA-specific immune response in patients affected by malignant diseases of different histology. Diverse strategies are currently utilized for the in vivo administration of therapeutic CTA in the clinic or for the generation of more powerful vaccinating tools at pre-clinical level (dos Santos N. R. et al., *Cancer Res.*, 60: 1654-1662, 2000; Weber J. et al., *Cancer Res.*, 54: 1766-1771, 1994) as the person expert in the art is aware of. Noteworthy, mainly due to a number of technical and practical limitations, only a limited number of immunogenic epitopes of specific CTA, or single whole CTA protein are currently utilized in the clinic for the therapeutic purposes. Following is a list including the main strategies already utilized, or hypothesised so far, to administer CTA to cancer patients; it should also be emphasised that identical strategies are utilized to administer to patients TAA that belong to the other classes of so far known TAA, and that different adjuvants and/or carriers are sometimes utilized to potentiate the immunogenicity of therapeutic agents.

- Synthetic peptides representing immunogenic epitope(s) of single or multiple CTA recognized by CD8+ T cells (Conference on Cancer Vaccines, Eds. Ferrantini M. and Belardelli F., Rome-Italy, Nov. 15-16, 1999.
- Liposome-encapsulated synthetic peptides representing immunogenic epitope(s) of single or multiple CTA (Steller M. A. et al., *Clin. Cancer Res.*, 4: 2103-2109, 1998).
- Whole synthetic protein of a single CTA (Conference on Cancer Vaccines, Eds. Ferrantini M. and Belardelli F., Rome-Italy, Nov. 15-16, 1999.
- Recombinant viral vectors expressing epitopes of single or multiple CTA recognized by CD8+ T cells (Jenne L. et al., *Trends Immunol.*, 22:102-107, 2001).
- Naked DNA shooting (Park J. H. et al., *Mol. Cells*, 9: 384-391, 1999).
- Autologous PBMC/macrophages loaded ex vivo with synthetic peptides representing epitopes of single or multiple CTA recognized by CD8+ T cells (Conference on Cancer Vaccines, Eds. Ferrantini M. and Belardelli F., Rome-Italy, Nov. 15-16, 1999).
- Autologous dendritic cells loaded ex vivo with synthetic peptides representing epitopes of single or multiple CTA recognised by CD8+ T cells or loaded with whole synthetic protein of a single CTA, or loaded with whole tumour cell preparations (Conference on Cancer Vaccines, Eds. Ferrantini M. and Belardelli F., Rome-Italy, Nov. 15-16, 1999 Jenne L. et al., *Trends Immunol.*, 22:102-107, 2001).
- Autologous dendritic cells transfected or transduced ex vivo with DNA/RNA to express full-length CTA or fused with whole tumor cells (Jenne L. et al., *Trends Immunol.*, 22:102-107, 2001);
- Autologous T lymphocytes transfected or transduced ex vivo with DNA/RNA to express full-length CTA.

As far as autologous cancer vaccines, which the present invention refers to as the main object, a number of patent references may be cited. WO 99/42128 discloses methods for determining the HLA transcription or expression profile of a solid tumor, for selection of appropriate treatments and/or for monitoring progress of the tumor. The purpose of this reference is to inhibit some isoforms of HLA-G in order to increase the native antitumor response. The method comprises extracting cells from a tumor sample, lysing them and reacting the lysate with antibodies directed against HLA Class I antigens.

DE 29913522 provides an apparatus for preparing a cancer vaccine by submitting tumor cells extracted from a patient to pressures of 200-9000 bar, in order to kill or damage the cells while leaving their surface intact then reinjecting the cells to the patient.

WO 00/02581 discloses a telomerase protein or peptide, capable of inducing a T cell response against an oncogene or mutant tumor suppressor protein or peptide. Said peptides are used for a cancer vaccine.

WO 00/18933 discloses DNA constructs causing expression of functionally inactive, altered antigens which are unaltered with respect to the efficiency of transcription and translation of DNA, RNA or the generation of antigenic peptides. The patient affected by cancer is treated by the administration of the RNA or plasmid DNA encoding an altered human cancer associated antigen, in particular PSMA antigen. In a different embodiment, autologous dendritic cells that have been exposed in vitro to the RNA or the plasmid DNA are used as vaccine.

WO 00/20581 discloses a cancer vaccine comprising a new isolated MAGE-A3 human leukocyte antigen (HLA) class II-binding peptide. The peptide can also be used to enrich selectively a population of T lymphocytes with CD4+ T lymphocytes specific the said peptide. Said enriched lymphocytes are also used as cancer vaccine.

WO 00/25813 discloses universal Tumor-Associated Antigen (TAA) binding to a major histocompatibility complex molecule. The method of treatment comprises administering a nucleic acid molecule encoding the TAA, which is processed by an antigen-presenting cell which activates cytotoxic lymphocytes and kills cells expressing TAA. Other than the specific hTERT peptide, the identification of different TAAs is enabled by a complex computer-aided method synthesis of the computer-designed peptide and biological assays for confirmation of the usefulness of the peptide.

WO 00/26249 discloses fragments of human WT-1 protein or human gata-1 protein. These peptide fragments are used for cancer vaccine through activation of cytotoxic T lymphocytes (CTL).

U.S. Pat. No. 6,077,519 provides a cancer vaccine comprising a composition of T cell epitopes recovered through acid elution of epitopes from tumor tissue.

WO 00/46352 provides a cancer vaccine comprising human T lymphocytes that express a functional CD86 molecule. T lymphocytes are obtained by subjecting T cells to at least two sequential stimuli, each involving at least one activator (an antibody anti CD2, 3 or 28) and a cytokine (interleukine) that stimulates T cell proliferation.

Coral S. et al. *Journal of Immunotherapy* 22(1):16-24, 1999, teach that the immunogenic potential of melanoma cells and their recognition by the host's cytotoxic cells depend on the presence and on the level of expression of Human Leukocytic Antigen (HLA) class I antigens, costimulatory molecules and melanoma-associated antigens (MAA) on neoplastic cells. There may be a suggestion that 5-AZA-CdR for use in active and/or passive specific immunotherapy for human melanoma through its systemic administration might enhance melanoma cells recognition by cytotoxic cells.

Momparler, *Anticancer Drugs Apr;* 8(4):358-68, 1997, mentions 5-AZA-CdR as chemotherapic.

Shichijo S. et al *Jpn. J. Cancer Res.* 87, 751-756, July 1996, investigated whether the demethylating agent 5-AZA-CDR induces MAGE 1, 2, 3 and 6 in normal and malignant lymphoid cells in order to better understand the mechanisms of their expression in the cells. The authors showed the induction of investigated CTA in selected samples tested and discussed that demethylation is not a sufficient stimulus to induce MAGE genes in all cases and that their results should lead to a better understanding of mechanisms of MAGE genes expression in cells. No perspective therapeutic implications were suggested.

ABSTRACT OF THE INVENTION

It has now been found a method of generation of antigen presenting cells, comprising:

a) collecting said cells from a subject, b) activating said collected cells;

c) culturing and optionally expanding ex vivo said activated cells;

d) treating said cultured and optionally expanded cells with DNA hypomethylating agents so that said cells concomitantly express multiple tumor associated antigens.

The cells obtainable according to the method of the present invention, as well as the cellular components thereof whether alone or in combination with said cells, are useful for prevention and treatment, in particular in a mammal, human beings included, of malignancies of different histotype that constitutively express one or more of the multiple tumor associated antigens that are expressed in said cells.

In the foregoing of the present invention, said cells are briefly named ADHAPI-Cells.

Most conveniently, the cells obtainable from the method above mentioned are used in the form of a cancer vaccine.

In the foregoing, the present invention shall be disclosed in detail also by means of examples and figures, wherein:

FIG. 1 shows the proliferation of autologous (aMLR) PBMC (R) stimulated with ADHAPI-Cells/B-EBV or control B-EBV cells (S);

FIG. 2 shows the proliferation of autologous (aMLR) PBMC (R) stimulated with ADHAPI-Cells/PWM-B or control PWM-B cells (S);

FIG. 3 shows the proliferation of autologous (aMLR) PBMC (R) stimulated with ADHAPI-Cells/CD40L-B or control CD40L-B cells (S);

FIG. 4 shows the proliferation of autologous (aMLR) PBMC (R) stimulated with ADHAPI-Cells/PWM-PBMC or control PWM-PBMC cells (S);

FIG. 5 shows the proliferation of autologous (aMLR) PBMC (R) stimulated with ADHAPI-Cells/PHA-PBMC and control PHA-PBMC;

FIG. 6 shows the proliferation of autologous (aMLR) PBMC (R) stimulated with ADHAPI-Cells/PHA-+PWM-PBMC or control PHA-+PWM-PBMC (S);

DETAILED DISCLOSURE OF THE INVENTION

According to the present invention, there is virtually no limit as to the type of cells that can be treated in order to generate the antigen-presenting cells, provided that they are suitably activated and treated with a hypomethylating agent.

According to the present invention, the cells are collected from a subject, in particular a mammal, more in particular a human. In a possible embodiment of the present invention, said human is a cancer patient.

In a first preferred embodiment of the present invention, antigen-presenting cells obtainable by the method above described are immune cells.

In a second preferred embodiment of the present invention, antigen-presenting cells obtainable by the method above described are non-immune cells.

The cells obtainable according to present invention can express shared immunodominant cancer antigens or can express shared not immunodominant cancer antigens.

In certain specific embodiments of the present invention, cells suitable for the method herein disclosed are:

Epstein-Barr virus-immortalized, DNA hypomethylating agent-treated B-lymphoblastoid cell lines, generated from peripheral blood mononuclear cells (PBMC) of cancer patients in advanced stage of disease or healthy subjects (ADHAPI-Cells/B-EBV).

Pokeweed mitogen (PWM)-activated, DNA hypomethylating agent-treated B-lymphocytes, generated from B-lymphocytes purified from PBMC of cancer patients in advanced stage of disease or healthy subjects (ADHAPI-Cells/PWM-B).

CD40 activated, DNA hypomethylating agent-treated B-lymphocytes, generated from B-lymphocytes purified from PBMC of cancer patients in advanced stage of disease or healthy subjects (ADHAPI-Cells/CD40-B).

Pokeweed mitogen (PWM)-activated, DNA hypomethylating agent-treated PBMC, generated from purified PBMC of cancer patients in advanced stage of disease or healthy subjects (ADHAPI-Cells/PWM-PBMC)

Phytohemagglutinin (PHA)+recombinant human interleukin-2 (rhIL-2)-activated, DNA hypomethylating agent-treated PBMC, generated from purified PBMC of cancer patients in advanced stage of disease or healthy subjects (ADHAPI-Cells/PHA-rhIL2-PBMC)

Phytohemagglutinin (PHA)+recombinant human interleukin-2 (rhIL-2)+pokeweed mitogen (PWM)-activated, DNA hypomethylating agent-treated PBMC, generated from purified PBMC of cancer patients in advanced stage of disease or healthy subjects (ADHAPI-Cells/PHA-rhIL2-PWM-PBMC)

Dendritic cells, monocytes, macrophages.

CD34+ cells, fibroblasts, stem cells, fibroblasts and cheratinocytes.

The cells obtainable by the method according to the present invention are suitable for use as agents for the prevention and treatment of malignancies of different histotype that constitutively express one or more of cancer antigens, whether immunodominant or not immunodominant.

Another possible embodiment of the present invention is applicable to those cases wherein it is not wished or necessary to utilize the direct antigen presenting ability of vaccinating cells. In this case, vaccinating cells or their cellular components obtainable by the method of the present invention can be used as "reservoir" of pooled cancer antigens to vaccinate patients.

In a preferred embodiment of the present invention, the selected TAA are CTA.

This embodiment of the present invention offers to the skilled person the following advantages:

CTA are immunogenic since they include epitopes recognized by HLA class I-restricted CTA-specific CD8+ CTL.

CTA are immunogenic since they include epitopes recognized by HLA class II-restricted CTA-specific CD4+ T lymphocytes.

Selected CTA simultaneously include epitopes presented by HLA class I and by HLA class II antigens; thus, selected CTA can concomitantly induce CD8+ CTL and CD4+ T lymphocytes reactions.

CTA are not expressed in benign tissues with the exception of testis and placenta.

Different CTA can be concomitantly expressed in neoplastic cells of solid and hemopoietic malignancies, providing multiple therapeutic targets that are co-expressed on transformed cells.

Distinct CTA are homogeneously expressed among concomitant and sequential metastatic lesions of given patients.

Distinct CTA can be expressed in malignant tissues of different hystological origin providing common therapeutic targets shared by human neoplasia regardless of their specific hystotype.

Distinct CTA may encode for multiple immunogenic peptides presented in the context of different HLA class I and HLA class II allospecificities.

In a further embodiment of the present invention, histone deacetylase inhibitors can sinergize with DNA hypomethylating agents in inducing/up-regulating the expression of CTA, of HLA antigens and of co-stimulatory/ accessory molecules on neoplastic cells of different histology. In fact, DNA methylation and histone deacetylation act as synergistic layers for the epigenetic gene silencing in cancer (Fuks F. et al., *Nat. Genet.*, 24: 88-91, 2000), and a strong reactivation of selected hypermethylated genes, with tumor suppressor function, has been observed in colorectal carcinoma cells after treatment with histone deacetylase inhibitors, following an initial minimal DNA demethylation (Cameron E. E. et al., *Nat. Genet.*, 21: 103-107, 1999).

The activation step in the method according to the present invention is carried out following the general common knowledge, in any case reference can be made to *Current Protocols in Immunology*, Coligan J. E. et al. Eds, Wiley.

The demethylation treatment in the method according to the present invention is generally well-known and the literature generally reports the procedure, for further information see also Santini V. et al., *Ann. Intern. Med.*, 134: 573-586, 2001.

Hypomethylating agents, also known in the art as demethylating agents, useful for the purposes of the present invention are well known in the art. DNA demethylating agents are widely disclosed in the literature, see for example WO 01/29235, U.S. Pat. No. 5,851,773. A preferred DNA demethylating agent is 5-aza-cytidine or, more preferred, 5-aza-2'-deoxycytidine (5-AZA-CdR).

Antigen presenting cells according to the present invention are suitable for the preparation of cancer vaccines. In a preferred embodiment of the present invention, said vaccines are autologous vaccines.

In another preferred embodiment of the present invention, said vaccines are allogeneic vaccines. In this embodiment, the cells obtainable according to the method above disclosed may be used both as antigen presenting cells and as in the form of "reservoir" of pooled cancer antigens, whether as cells or cellular components thereof.

In a still further another embodiment of the present invention, the cells and/or the cellular components can be used in a method for generating effector immune cells, said effector immune cells being used for the preparation of a product useful in the well-known adoptive immunotherapy. In another embodiment of the present invention, the vaccine herein disclosed can be used in combination with a systemic pre-treatment of the cancer patient with a hypomethylating agent, for example decitabine. This embodiment may be performed with an article of manufacture, for example a kit, comprising a vaccine according to the present invention and a pharmaceutical composition suitable for systemic administration of a hypomethylating agent, for example decitabine.

Vaccines can be prepared according to techniques wellknow to the person skilled in this art, just resorting to the general common knowledge. For example, the patent references mentioned in the present description are a sufficient disclosure for the preparation of cancer vaccines, see for example WO 00/25813 or WO 00/46352.

The skilled person will have no difficulty in establishing the proper manner for using the vaccines according to the present invention, in particular as to the administration protocol.

The following examples further illustrate the present invention.

EXAMPLE 1

ADHAPI-Cells/B-EBV

PBMC Purification

PBMC were purified by standard Ficoll-Hypaque density gradient centrifugation from heparinized peripheral blood of cancer patients in advanced stage of disease or healthy subjects.

Generation of Autologous B-Lymphoblastoid Cell Lines by the Immortalization of PBMC with Epstein-Barr Virus (EBV)

B-EBV+ lymphoblastoid cell lines were generated by incubating PBMC with supernatant from B95.8 marmoset cell line at 37° C. in a 5% $CO_2$ humidified atmosphere, in RPMI 1640 medium supplemented with 10% heat-inactivated foetal calf serum (or human AB serum) and 2 mM L-glutamine.

Generation of ADHAPI-Cells/B-EBV and Control B-EBV Cells

B-EBV+ lymphoblastoid cell lines ($7.5 \times 10^5$ cells/ml) were cultured in RPMI 1640 medium supplemented with 10% heat-inactivated foetal calf serum (or 10% heat-inactivated human AB serum) and 2 mM L-glutamine at 37° C. in a 5% $CO_2$ humidified atmosphere, and pulsed four times with 1 μM 5-aza-2'-deoxycytidine (5-AZA-CdR) every 12 h; then, half of the culture medium was replaced with fresh medium and cultures were allowed to proceed for additional 48 h. Then cells were utilized for experimental procedures and/or frozen under viable conditions. Control cells (B-EBV cells) were cultured under similar experimental conditions but without pulses of 5-AZA-CdR.

Final Recovery of ADHAPI-Cells/B-EBV and Control B-EBV Cells

For the results, see Table 1.

Autologous Mixed Lymphocyte Reaction (aMLR) and MLR

ADHAPI-Cells/B-EBV and control B-EBV cells (stimulators=S) were collected, washed twice with Hanks' balanced salt solution (HBSS) and x-ray treated (75 Gy). For aMLR and MLR scalar concentrations (from $1\times10^6$ cells/ml to $6\times10^4$ cells/ml) of ADHAPI Cells/B-EBV or control B-EBV cells were added to autologous or allogeneic PBMC ($1\times10^6$ cells/ml) (responder=R) in Basal Iscove's medium supplemented with 10% heat-inactivated human AB serum, 2 mM L-glutamine, 100 U/ml penicillin, 100 µg/ml streptomycin sulphate, and seeded in 96 well U-bottom plates to a final volume of 200 µl/well. After a 24 h incubation at 37° C. in a 5%$CO_2$ humidified atmosphere, 100 µl of culture supernatant were collected and immediately stored at −80° C. until use for cytokine assay. Then, 100 µl of fresh medium were added to each well and cultures were allowed to proceed for additional five days, when cultures were pulsed O/N with $^3$H-TdR (1 µLCi/well); then plates were harvested and $^3$H-TdR incorporation by R cells was measured by a β-counter.

Proliferation of Autologous PBMC (R) Stimulated with ADHAPI-Cells/B-EBV or Control B-EBV Cells (S) in aMLR See FIG. 1.

Phenotypic Profile of ADHAPI-Cells/B-EBV and Control B-EBV Cells

See Table II for results.

RT-PCR Analysis of CTA Expressed by ADHAPI-Cells/B-EBV and Control B-EBV Cells

Experimental conditions and primers utilized to assess CTA expression on investigated cells were as follows:

for MAGE-1, -2, -3, -4 Brasseur, F., et al. *Int. J. Cancer* 63: 375-380, 1995; for GAGE 1-6 Van den Eynde, B., et al. *J. Exp. Med.* 182: 689-698, 1995; for NY-ESO-1 Stockert, E. et al. *J. Exp. Med.* 187: 265-270, 1998; for SSX-2; Sahin, U., et al. *Clin. Cancer Res.* 6: 3916-3922, 2000.

| 5-AZA-CdR | − | + |
|---|---|---|
| MAGE-1 | 0/4[a] | 4/4 |
| MAGE-2 | NT | NT |
| MAGE-3 | 0/4 | 4/4 |
| MAGE-4 | NT | NT |
| NY-ESO-1 | 0/4 | 4/4 |
| GAGE-1-6 | 0/4 | 4/4 |
| SSX-2 | 2/4 | 4/4 |

[a]posittive/tested;
NT, not tested;

ELISA Evaluation of IFN-γ Released by PBMC (R) Stimulated in aMLR by ADHAPI-Cells/B-EBV or Control B-EBV Cells (S)

See Table III for results.

EXAMPLE 2

ADHAPI-Cells/PWM-B

B-Lymphocyte Purification

PBMC were purified by standard Ficoll-Hypaque density gradient centrifugation from heparinized peripheral blood of cancer patients in advanced stage of disease or healthy subjects, and purified B lymphocytes were obtained by conventional E resetting technique utilizing neuraminidase-treated sheep red blood cells.

Generation of PWM-Activated B Cells

Purified B-Lymphocytes ($1.5\times10^6$ cells/ml) were added with PWM (3 µg/ml) and cultured for 48 h at 37° C. in a 5% $CO_2$ humidified atmosphere in Basal Iscove's medium supplemented with 10% heat-inactivated human AB serum, 2 mM L-glutamine, 100 U/ml penicillin, 100 µg/ml streptomycin sulphate.

Generation of ADHAPI-Cells/PWM-B and Control PWM-B Cells

PWM-activated B-Lymphocytes were pulsed four times with 1 µM 5-aza-2'-deoxycytidine (5-AZA-CdR) every 12 h; then, half of the culture medium was replaced with fresh medium and cultures were allowed to proceed for additional 48 h. Then cells were utilized for experimental procedures and/or frozen under viable conditions. Control cells (PWM-B) were cultured under similar experimental conditions but without pulses of 5-AZA-CdR.

Final Recovery of ADHAPI-Cells/PWM-B and Control PWM-B Cells

See Table I for results

Autologous Mixed Lymphocyte Reaction (aMLR) and MLR

ADHAPI-Cells/PWM-B and control PWM-B cells (stimulators=S) were collected, washed three times with Hanks' balanced salt solution supplemented with 0.5% α-methylmannopyranoside, and x-ray treated (30 Gy). For aMLR and MLR scalar concentrations (from $1\times10^6$ cells/ml to $6\times10^4$ cells/ml) of ADHAPI-Cells/PWM-B or control PWM-B cells were added to autologous or allogeneic PBMC ($1\times10^6$ cells/ml) (responder=R) in Basal Iscove's medium supplemented with 10% heat-inactivated human AB serum, 2 mM L-glutamine, 100 U/ml penicillin, 100 µg/ml streptomycin sulphate, and seeded in 96 well U-bottom plates to a final volume of 200 µl/well. After a 6 day incubation at 37° C. in a 5% $CO_2$ humidified atmosphere, 100 µl of culture supernatant were collected from each well and immediately stored at −80° C. until use for cytokine assay. Then, 100 µl of fresh medium were added to each well and cultures were pulsed O/N with $^3$H-TdR (1 µCi/well); then, plates were harvested and $^3$H-TdR incorporation by R cells was measured by a β-counter.

Phenotypic Profile of ADHAPI-Cells/PWM-B and Control PWM-B Cells

See Table II for results

RT-PCR Analysis of CTA Expressed by ADHAPI-Cells/PWM-B and Control PWM-B Cells

| 5-AZA-CdR | − | + |
|---|---|---|
| MAGE-1 | 0/4[a] | 4/4 |
| MAGE-2 | 0/4 | 4/4 |
| MAGE-3 | 0/4 | 4/4 |
| MAGE-4 | 0/4 | 4/4 |
| NY-ESO-1 | 0/4 | 4/4 |
| GAGE-1-6 | 0/4 | 4/4 |
| SSX-2 | 1/4 | 4/4 |

[a]positive/tested;
NT, not tested.

Proliferation of Autologous PBMC (R) Stimulated with ADHAPI-Cells/PWM-B or Control PWM-B Cells (S) in aMLR See FIG. 2 for results.

ELISA Evaluation of IFN-γ Released by Allogeneic (MLR) and Autologous (aMLR) PBMC (R) Stimulated with ADHAPI-Cells/PWM-B or Control PWM-B Cells (S)

See Table III for results.

EXAMPLE 3

ADHAPI-Cells/CD40LB

PBMC Purification

PBMC were purified by standard Ficoll-Hypaque density gradient centrifugation from heparinized or acid citrate dextrose (ACD)-anticoagulated peripheral blood of cancer patients in advanced stage of disease or healthy subjects.

Generation of NIH3T3-CD40L-activated PBMC

PBMC ($2 \times 10^6$ cells/ml) were co-cultured with semiconfluent, x-ray treated (75 Gy) NIH3T3-CD40L at 37° C. in a 5% $CO_2$ humidified atmosphere, in Basal Iscove's medium supplemented with 10% heat-inactivated human AB serum, 2 mM L-glutamine, 2 ng/ml recombinant human (rh) interleukin 4 (rhIL-4), 50 µg/ml human transferrin, 5 µg/ml rh insulin, $5.5 \times 10^{-7}$ M cyclosporin A (CsA), 100 U/ml penicillin, and 100 µg/ml streptomycin sulphate (complete medium). After six days of incubation, PBMC were collected, washed twice with HBSS, resuspended at $1 \times 10^6$ cells/ml in complete medium and co-cultured for additional 3 days at 37° C. in a 5% $CO_2$ humidified atmosphere with NIH3T3-CD40L freshly prepared as described above. This procedure was repeated every 2-3 days to a maximum culture time of 16-18 days.

Generation of ADHAPI-Cells/CD40L-B and Control CD40L-B Cells

After 16-18 days of culture, activated PBMC were harvested and restimulated with NIH3T3-CD40L as described above; after an O/N incubation at 37° C. in a 5% $CO_2$ humidified atmosphere, cultures were pulsed four times with 1 µM 5-aza-2'-deoxycytidine (5-AZA-CdR) every 12 h; then, cells were harvested and restimulated with NIH3T3-CD40L as described above and cultures were allowed to proceed for additional 48 h. Then cells were utilized for experimental procedures and/or frozen under viable conditions. Control cells (CD40L-B cells) were cultured under similar experimental conditions but without pulses of 5-AZA-CdR.

Final Recovery of ADHAPI-Cells/CD40L-B and Control CD40L-B Cells

See Table I for results.

Autologous Mixed Lymphocyte Reaction (aMLR) and MLR

ADHAPI-Cells/CD40L-B and control CD40L-B cells (stimulators=S) were collected, washed three times with Hanks' balanced salt solution and x-ray treated (50 Gy). For aMLR and MLR scalar concentrations (from $1 \times 10^6$ cells/ml to $6 \times 10^4$ cells/ml) of ADHAPI-Cells/CD40L-B or control CD40L-B cells were added to autologous or allogeneic PBMC ($1 \times 10^6$ cells/ml) (responder=R) in Basal Iscove's medium supplemented with 10% heat-inactivated human AB serum, 2 mM L-glutamine, 100 U/ml penicillin, 100 µg/ml streptomycin sulphate, and seeded in 96 well U-bottom plates to a final volume of 200 µl/well. After a 24 h incubation at 37° C. in a $CO_2$ humidified atmosphere, 100 µl of culture supernatant were collected and immediately stored at −80° C. until use for cytokine assay. Then, 100 µl of fresh medium were added to each well and cultures were allowed to proceed for additional 5 days when cultures were pulsed O/N with $^3$H-TdR (1 µCi/well); then plates were harvested and 3H-TdR incorporation by R cells was measured by a β-counter.

Phenotypic Profile of ADHAPI-Cells/CD40L-B and Control CD40L-B Cells

See Table II for results.

RT-PCR Analysis of CTA Expressed by ADHAPI-Cells/CD40L-B and Control CD40L-B Cells

| 5-AZA-CdR | − | + |
|---|---|---|
| MAGE-1 | 0/10[a] | 10/10 |
| MAGE-2 | 0/10 | 9/10 |
| MAGE-3 | 0/11 | 10/11 |
| MAGE-4 | 0/11 | 11/11 |
| NY-ESO-1 | 0/14 | 14/14 |
| GAGE-1-6 | 0/14 | 14/14 |
| SSX-2 | 0/14 | 13/14 |

[a]positive/tested.

Proliferation of Autologous (aMLR) PBMC (R) Stimulated with ADHAPI-Cells/CD40L-B or Control CD40L-B Cells (S) in aMLR See FIG. 3 for results.

ELISA Evaluation of IFN-γ Released by PBMC (R) Stimulated in aMLR by ADHAPI-Cells/CD40L-B or Control CD40L-B Cells (S)

See Table III for results.

EXAMPLE 4

ADHAPI-Cells/PWM-PBMC

PBMC Purification

PBMC were purified by standard Ficoll-Hypaque density gradient centrifugation from heparinized peripheral blood of cancer patients in advanced stage of disease or healthy subjects.

Generation of PWM-activated PBMC

PBMC ($1.5 \times 10^6$ cells/ml) were added with PWM (3 µg/ml) and cultured for 48 h at 37° C. in a 5% $CO_2$ humidified atmosphere in Basal Iscove's medium supplemented with 10% heat-inactivated human AB serum, 2 mM L-glutamine, 100 U/ml penicillin, 100 µg/ml streptomycin sulphate.

Generation of ADHAPI-Cells/PWM-PBMC and Control PWM-PBMC Cells

PWM-activated PBMC were pulsed four times with 1 µM 5-aza-2'-deoxycytidine (5-AZA-CdR) every 12 h; then, half of the culture medium was replaced with fresh medium and cultures were allowed to proceed for additional 48 h. Then cells were utilized for experimental procedures and/or frozen under viable conditions. Control cells (PWM-PBMC) were cultured under similar experimental conditions but without pulses of 5-AZA-CdR.

Final Recovery of ADHAPI-Cells/PWM-PBMC and Control PWM-PBMC Cells

See Table I for results.

Autologous Mixed Lymphocyte Reaction (aMLR) and MLR

ADHAPI-Cells/PWM-PBMC and control PWM-PBMC Cells (stimulators=S) were collected, washed three times with Hanks' balanced salt solution supplemented with 0.5% α-methylmannopyranoside, and x-ray treated (30 Gy). For aMLR and MLR scalar concentrations (from $1 \times 10^6$ cells/ml to $6 \times 10^4$ cells/ml) of ADHAPI-Cells/PWM-PBMC or control PWM-PBMC cells were added to autologous or allogeneic PBMC ($1 \times 10^6$ cells/ml) (responder=R) in Basal Iscove's medium supplemented with 10% heat-inactivated human AB serum, 2 mM L-glutamine, 100 U/ml penicillin, 100 µg/ml streptomycin sulphate, and seeded in 96 well U-bottom plates to a final volume of 200 µl/well. After a 6 day incubation at 37° C. in a 5% $CO_2$ humidified atmosphere, 100 µl of culture supernatant were collected from each well and immediately stored at −80° C. until use for cytokine 100 µl of fresh medium were added to each well were pulsed O/N with $^3$H-TdR (1 µCi/well); then harvested and $^3$H-TdR incorporation by R cells was measured by a β-counter.

Phenotypic Profile of ADHAPI-Cells/PWM-PBMC and Control PWM-PBMC Cells

See Table II for results.

RT-PCR Analysis of CTA Expressed by ADHAPI-Cells/PWM-PBMC and Control PWM-PBMC Cells

| 5-AZA-CdR | − | + |
|---|---|---|
| MAGE-1 | 0/4[a] | 4/4 |
| MAGE-2 | 0/4 | 3/4 |
| MAGE-3 | 0/4 | 4/4 |
| MAGE-4 | 1/4 | 3/4 |
| NY-ESO-1 | 0/4 | 4/4 |
| GAGE-1-6 | 0/4 | 3/4 |
| SSX-2 | 0/4 | 3/4 |

[a]positive/tested;
NT, not tested.

Proliferation of Autologous (aMLR) PBMC (R) Stimulated with ADHAPI-Cells/PWM-PBMC or Control PWM-PBMC Cells (S) in aMLR See FIG. 4 for results.

ELISA Evaluation of IFN-γ Released by Autologous PBMC -(R) Stimulated in aMLR by ADHAPI-Cells/PWM-PBMC or Control PWM-PBMC Cells (S)

See Table III for results.

EXAMPLE 5

ADHAPI-Cells/PHA-PBMC

PBMC Purification

PBMC were purified by standard Ficoll-Hypaque density gradient centrifugation from heparinized peripheral blood of cancer patients in advanced stage of disease or healthy subjects.

Generation of PHA-activated PBMC

PBMC (1.5×10$^6$ cells/ml) were added with PHA-M (10 µg/ml) and 100 UI/ml rhIL-2, and cultured for 48 h at 37° C. in a 5% CO$_2$ humidified atmosphere in RPMI 1640 medium supplemented with 10% heat-inactivated foetal calf serum (or in Basal Iscove's medium supplemented with 10% heat-inactivated human AB serum), 2 mM L-glutamine, 100 U/ml penicillin, 100 µg/ml streptomycin sulphate (complete medium).

Generation of ADHAPI-Cells/PHA-PBMC and Control PHA-PBMC

PHA-activated PBMC were pulsed four times with 1 µM 5-aza-2'-deoxycytidine (5-AZA-CdR) every 12 h; then, half of the culture medium was replaced with fresh complete medium without PHA-M and cultures were allowed to proceed for additional 48 h. Then cells were utilized for experimental procedures and/or frozen under viable conditions. Control cells (PHA-PBMC) were cultured under similar experimental conditions but without pulses of 5-AZA-CdR.

Final Recovery of ADHAPI-Cells/PHA-PBMC and Control PHA-PBMC

See Table I for results.

Autologous Mixed Lymphocyte Reaction (aMLR) and MLR

ADHAPI-Cells/PHA-PBMC and Control PHA-PBMC (stimulators=S) were collected, washed three times with Hanks' balanced salt solution supplemented with 0.5% α-methylmannopyranoside, and x-ray treated (50 Gy). For aMLR and MLR scalar concentrations (from 1×10$^6$ cells/ml to 6×10$^4$ cells/ml) of ADHAPI-Cells/PHA-PBMC or control PHA-PBMC were added to autologous or allogeneic PBMC (1×10$^6$ cells/ml) (responder=R) in Basal Iscove's medium supplemented with 10% heat-inactivated human AB serum, 2 mM L-glutamine, 100 U/ml penicillin, 100 µg/ml streptomycin sulphate and seeded in 96 well U-bottom plates to a final volume of 200 µl/well. After a 24 h incubation at 37° C. in a 5% CO$_2$ humidified atmosphere, 100 µl of culture supernatant were collected from each well and immediately stored at −80° C. until use for cytokine assay. Then, 100 µl of fresh medium were added to each well and cultures were allowed to proceed for additional 5 days when cultures were pulsed O/N with 3H-TdR (1 µCi/well); then, plates were harvested and $^3$H-TdR incorporation by R cells was measured by a β-counter.

Phenotypic Profile of ADHAPI-Cells/PHA-PBMC and Control PHA-PBMC

See Table II for results.

RT-PCR Analysis of CTA Expressed by ADHAPI-Cells/PHA-PBMC and Control PHA-PBMC

| 5-AZA-CdR | − | + |
|---|---|---|
| MAGE-1 | 0/12[a] | 12/12 |
| MAGE-2 | 0/3 | 3/3 |
| MAGE-3 | 0/12 | 12/12 |
| MAGE-4 | 0/4 | 4/4 |
| NY-ESO-1 | 0/6 | 6/6 |
| GAGE-1-6 | 0/4 | 4/4 |
| SSX-2 | 0/6 | 6/6 |

[a]positive/tested;
NT, not tested.

Proliferation of Autologous PBMC (R) Stimulated with ADHAPI-Cells/PHA-PBMC and Control PHA-PBMC in aMLR See FIG. 5 for results.

ELISA Evaluation of IFN-γ (Released by Allogeneic (MLR) and Autologous (aMLR) PBMC (R) Stimulated with ADHAPI-Cells/PHA-PBMC or Control PHA-PBMC(S)

See Table III for results.

EXAMPLE 6

ADHAPI-Cells/PHA+PWM-PBMC

PBMC Purification

PBMC were purified by standard Ficoll-Hypaque density gradient centrifugation from heparinized or ACD-anticoagulated peripheral blood of cancer patients in advanced stage of disease or healthy subjects.

Generation of PHA+PWM-activated PBMC

PBMC (1.5×10$^6$ cells/ml) were added with PHA-M (10 µg/ml), PWM (3 µg/ml), 100 UI/ml rhIL-2 and cultured for 48 h at 37° C. in a 5% CO$_2$ humidified atmosphere in Basal Iscove's medium supplemented with 10% heat-inactivated human AB serum (or with 10% heat-inactivated autologous serum), 2 mM L-glutamine, 100 U/ml penicillin, 100 µg/ml streptomycin sulphate (complete medium).

Generation of ADHAPI-Cells/PHA+PWM-PBMC and Control PHA+PWM-PBMC

PHA+PWM-activated PBMC were pulsed four times with 1 µM 5-aza-2'-deoxycytidine (5-AZA-CdR) every 12 h; then, half of the culture medium was replaced with fresh complete medium without PHA or PWM and cultures were allowed to proceed for additional 48 h. Then cells were utilized for experimental procedures and/or frozen under viable conditions. Control cells (PHA+PWM-PBMC) were cultured under similar experimental conditions but without pulses of 5-AZA-CdR.

Final Recovery of ADHAPI-Cells/PHA+PWM-PBMC and Control PHA+PWM-PBMC

See Table I for results.

Autologous Mixed Lymphocyte Reaction (aMLR) and MLR

ADHAPI-Cells/PHA+PWM-PBMC and control PHA+PWM-PBMC (stimulators=S) were collected, washed three times with Hanks' balanced salt solution supplemented with 0.5% α-methylmannopyranoside, and x-ray treated (50 Gy). For aMLR and MLR scalar concentrations (from $1\times10^6$ cells/ml to $6\times10^4$ cells/ml) of ADHAPI-Cells/PHA-rhIL2-+PWM-PBMC or control PHA+PWM-PBMC were added to autologous or allogeneic PBMC ($1\times10^6$ cells/ml) (responder=R) in Basal Iscove's medium supplemented with 10% heat-inactivated human AB serum, 2 mM L-glutamine, 100 U/ml penicillin, 100 μg/ml streptomycin sulphate, and seeded in 96 well U-bottom plates to a final volume of 200 μl/well. After a 6 day incubation at 37° C. in a 5% $CO_2$ humidified atmosphere, 100 μl of culture supernatant were collected from each well and immediately stored at −80° C. until use for cytokine assay. Then, 100 μl of fresh medium were added to each well and cultures were pulsed O/N with $^3$H-TdR (1 μCi/well); then, plates were harvested and $^3$H-TdR incorporation by R cells was measured by a β-counter.

Phenotypic Profile of ADHAPI-Cells/PHA+PWM-PBMC and Control

PHA+PWM-PBMC

See Table II for results.

RT-PCR Analysis of CTA Expressed by ADHAPI-Cells/PHA+PWM-PBMC and Control PHA+PWM-PBMC

| 5-AZA-CdR | − | + |
|---|---|---|
| MAGE-1 | 0/7[a] | 7/7 |
| MAGE-2 | 0/7 | 7/7 |
| MAGE-3 | 0/7 | 7/7 |
| MAGE-4 | 0/7 | 7/7 |
| NY-ESO-1 | 0/7 | 7/7 |
| GAGE-1-6 | 0/7 | 7/7 |
| SSX-2 | 0/7 | 7/7 |

[a]positive/tested.

Proliferation of Autologous (aMLR) PBMC (R) Stimulated with ADHAPI-Cells/PHA+PWM-PBMC or Control PHA+PWM-PBMC in aMLR See FIG. 6 for results.

ELISA Evaluation of IFN-γ Released by Allogeneic (MLR) and Autologous (aMLR) PBMC (R) Stimulated with ADHAPI-Cells/PHA+PWM-PBMC or Control PHA+PWM-PBMC (S).

See Table III for results.

In Vivo Tumorigenicity of ADHAPI-Cells

Single subcutaneous xenografts of viable ADHAPI Cells/PHA-rhIL2-PWM-PBMC ($12\times10^6$) and their control cells ($14\times10^6$), ADHAPI-Cells /CD40L-B ($8\times10^6$) and their control cells ($8\times10^6$) or x-ray-treated (30 Gy) ADHAPI-Cells/PHA-rhIL2 PWM-PBMC ($12\times10^6$) and their control cells ($14\times10^6$), x-ray treated (50 Gy) ADHAPI-Cells /CD40L-B ($15\times10^6$) and their control cells ($18\times10^6$), neither induced tumor formation at injection or distant (clinically explorable) sites, nor affected general health and weight of BALB/c nu/nu mice 180 days after ADHAPI-Cells administration. Repeated subcutaneous xenografts of viable ADHAPI-Cells/B-EBV ($5\times10^6/1^{st}$ injection; $1\times10^7/2^{nd}$ and subsequent injections) and control B-EBV cells ($5\times10^6/1^{st}$ injection; $1\times10^7/2^{nd}$ and subsequent injections) or x-ray-treated ADHAPI-Cells/B-EBV (75 Gy) ($5\times10^6/1^{st}$ injection; $1\times10^7/2^{nd}$ and subsequent injections) and x-ray-treated (75 Gy) control B-EBV cells ($5\times10^6/1^{st}$ injection; $1\times10^7/2^{nd}$ and subsequent injections), at day 0, 33, 63 and 96, neither induced tumor formation at injection or distant (clinically explorable) sites, nor affected general health and weight of BALB/c nu/nu mice 180 days after the first administration. General health and weight of ADHAPI-Cells-treated animals was comparable to control animals, untreated or grafted with B-EBV cells.

Advantages of ADHAPI-Cells as Polyvalent Cellular CTA Vaccines

As compared to the main strategies already utilized, or so far hypothesised, to most effectively administer known CTA to cancer patients, ADHAPI-Cells represent a totally new and innovative approach, and comprise a number of prominent/remarkable advantages. Among these:

ADHAPI-Cells vs Not Genetically-Modified Cellular CTA Vaccines

ADHAPI-Cells are new and unique APC vaccines as they concomitantly express multiple/all methylation-regulated CTA; being endogenously synthesised, CTA can directly and simultaneously access both HLA class I and HLA class II antigen processing pathways within ADHAPI-Cells (Jenne L. et al., *Trends Immunol.*, 22:102-107, 2001).

Thus, due to their constitutive cell membrane expression of both HLA class I and HLA class II antigens, ADHAPI-Cells can concomitantly present immunogenic epitopes of endogenously synthesised CTA both to CD8+ and to CD4+ T autologous lymphocytes; therefore, ADHAPI-Cells can simultaneously induce/amplify a CTA-directed CTL and humoral immune responses. Additionally, ADHAPI-Cells may express and present to host's T cells methylation-regulated CTA that have not been identified and characterized yet (as well as not immunodominant epitopes of known and still unknown CTA).

Opposite to ADHAPI-Cells, synthetic CTA peptide(s)-pulsed, synthetic CTA whole protein-pulsed, or whole tumor cell preparations-pulsed autologous APC vaccines (e.g., dendritic cells, PBMC), as well as electrofusion-generated tumor cell dendritic cell hybrids (Kugler A. et al., *Nat. Med.*, 6: 332-336, 2000. Tureci O. et al., *Cancer Res.*, 56: 4766-4772, 1996. Eds), share major limitations including: i) the unknown fate in vivo of the ex vivo-loaded synthetic CTA peptide(s), of whole synthetic CTA protein or of tumor-derived CTA, which may significantly affect the longevity of antigen presentation to host's immune system; ii) limited amounts of synthetic CTA peptide(s), of whole synthetic CTA protein or of tumor-derived CTA that can be loaded ex vivo onto HLA class I and/or HLA class II antigens of cellular vaccines, which may significantly hamper the immunogenicity of administered CTA; iii) the restriction by the patient's HLA phenotype, and the still relatively limited number of known HLA class I antigens- and even more HLA class II antigens restricted immunogenic epitopes of so far identified CTA; iv) availability of adequate amounts of fresh tumor tissue, that should also be sufficiently representative of the diverse CTA expressed in neoplastic lesions (Jenne L. et al., *Trends Immunol.*, 22:102-107, 2001).

The expression of endogenously synthesised CTA by ADHAPI-Cells is long lasting; thus, at variance with ex vivo synthetic CTA peptide(s)-pulsed or synthetic CTA whole protein-pulsed or whole tumor cell preparations-pulsed autologous APC vaccines, ADHAPI-Cells can provide a prolonged stimulation in vivo of hosts immune response and with a lower number of administrations to patients. This hypothesis is reinforced by the foreseen possibility to administer ADHAPI-Cells as a viable, not x-ray-treated, cellular vaccines due to their absence of long term tumorigenicity in vivo. Furthermore, once ADHAPI-Cells would undergo physiological death in vivo, they could still act as a "reservoir" of endogenously synthesised CTA peptides and proteins, that could further and efficiently boost the presentation of HLA class I-restricted epitopes of CTA to CD8+ T cells by patient's dendritic cells, through the immunologic mechanism of cross-priming, as well as the presentation of HLA class II-restricted epitopes of CTA to CD4+ T cells, through the well-defined exogenous pathway of antigen processing.

ADHAPI-Cells retain their APC function; in fact, they efficiently stimulate the proliferation and IFN-γ release of autologous and allogeneic PBMC; furthermore, ADHAPI-Cells are in most instances more potent stimulators as compared to their respective control cells. In this respect, it is relevant that in addition to CTA, ADHAPI-Cells may concomitantly express higher levels of HLA class I antigens and/or of different co-stimulatory/accessory molecules as compared to their respective control cells. These evidences clearly represent a great advantage of ADHAPI-Cells as autologous cellular vaccines, compared to autologous tumor cells that are poorly immunogenic, and do not constitutively express several co-stimulatory/accessory molecules. Furthermore, as compared to ex vivo-generated and expanded autologous dendritic cells, ADHAPI-Cells vaccines are generated by fully mature and immunocompetent APC; this aspect overcomes the potential limitation represented by the maturation stage of dendritic cells utilized for the generation of cellular vaccines, which may influence their tolerogenic rather than immunogenic potential.

As compared to other cellular vaccines, the ex vivo generation of ADHAPI-Cells vaccines, that concomitantly express multiple/all methylation-regulated CTA, is simple, in most cases rapid, does not require cumbersome in vitro cellular manipulations, does not involve genetic manipulations, does not require autologous tumor tissue, and it is highly reproducible both from PBMC of healthy individuals and cancer patients.

Furthermore, close to 100% of ADHAPI-Cells preparations express all investigated CTA that are demethylation-inducible in APC. Due to these characteristics, the generation of ADHAPI-Cells vaccines is easier to standardize and to control for quality (for example by flow cytometry for selected cell surface molecules and RT-PCR for selected CTA) and potency (for example by quantitative RT-PCR for selected CTA). Additionally, compared to other cellular vaccines that to date must be freshly prepared each time they must be administered to patients, thus generating obvious inter-preparations variability (e. g., cellular viability, phenotypic profile of vaccinating cells, amount of loaded synthetic CTA peptide(s) or synthetic CTA whole protein or of whole tumor cell preparations, efficiency of generation of tumor cell-dendritic cell hybrids by electrofusion), ADHAPI-Cells vaccines, once prepared and checked for viability, quality and potency, can be aliquoted, appropriately frozen, and stored under viable conditions until use for therapeutic purposes. Furthermore, since they do not require the availability of autologous tumor tissue to pulse autologous cellular vaccines or to generate tumor cell-dendritic cell hybrids ex vivo, and since they can be rapidly prepared in large number from repeated leukaphereses, ADHAPI-Cells vaccines represent a practically unlimited source of therapeutic agent for each patient.

In light of their concomitant expression of multiple/all methylation-regulated CTA that are endogenously synthesised, and that can directly and simultaneously access the HLA class I and HLA class II antigen-processing pathway, owing to their possibility to express and present to host's T cells methylation regulated CTA that have not been identified and characterized yet (as well as not immunodominant epitopes of known and still unknown CTA), and due to the still limited number of known HLA class I antigens- and HLA class II antigens-restricted immunogenic epitopes of so far identified CTA that can thus be utilized for therapeutic applications according to patient's HLA phenotype, an additional advantage of ADHAPI-Cells is that they are most likely able to concomitantly present known and still unknown immunogenic epitopes of different CTA in the context of any and multiple HLA class I and HLA class II allospecificities. Thus, as compared to synthetic CTA peptide(s)-pulsed or synthetic CTA whole protein-pulsed cellular vaccines, treatment with ADHAPI-Cells vaccines is not limited to patients with defined HLA phenotypes; hence, all cancer patients whose neoplastic lesions express one or more CTA can be candidate to treatment with ADHAPI-Cells vaccines, regardless of their HLA phenotype. In this respect, among the so far known CTA, one or more of them is generally expressed- in most investigated malignancies of different histotype; therefore, vaccination with ADHAPI-Cells is suitable in the large majority of cancer patients. A significant information is that MAGE, GAGE or NY-ESO-1 are expressed in 96% of human tumors (*Cancer Immunol. Immunother.* 50:3-15, 2001).

Compared to synthetic CTA peptide(s)-pulsed and synthetic CTA whole protein-pulsed cellular vaccines, in which limited amounts of protein(s) can be loaded ex vivo onto HLA class I and/or HLA class II antigens of cellular vaccines, significantly hampering the immunogenicity of administered CTA, and due to their concomitant expression of multiple all methylation-regulated CTA, ADHAPI-Cells vaccines can overcome the immunoselection of CTA-negative tumor variants occurring in the course of treatment against single or few CTA, and overcome the constitutively heterogeneous and sometimes down-regulated expression of distinct CTA occurring in specific neoplastic lesions.

ADHAPI-Cells vaccines are constituted by autologous functional APC that concomitantly express multiple/all known methylation-regulated CTA, and that most likely express still unidentified CTA whose expression is regulated by DNA methylation; furthermore, ADHAPI-Cells vaccines can be utilized in patients affected by CTA-positive tumors of different histotype. These functional and phenotypic features represent a clear advantage over currently utilized allogeneic tumor cell vaccines (e.g., lysates of whole pooled neoplastic cell lines or their non-purified extracts, shed antigens from pooled neoplastic cell lines). In fact, these tumor cell vaccines may not contain or may contain insufficient amounts of known and of still unknown immunologically-relevant CTA, contain irrelevant cellular components that may compete with CTA for immunological responses, may have increased toxicity being allogeneic, require efficient processing by patients' immune system, and can be utilized exclusively in patients affected by malignancies of the same histologic type.

ADHAPI-Cells vs Genetically Modified Cellular CTA Vaccines

The generation of ADHAPI-Cells does not involve the ex vivo genetic manipulations of autologous dendritic cells or of other autologous APC, that are required to produce genetically-modified cellular vaccines expressing selected CTA following transfection or transduction. Furthermore, as compared to ADHAPI/Cells, a number of limitations affect genetically-modified cellular vaccines; among these are: i) the relative low efficiency of available transfection methodologies; ii) the induction of cellular immune responses against antigens of the viral vectors utilized for cellular transduction, which leads to the destruction of genetically-modified vaccinating cells; iii) the presence of pre-existing or vaccination-induced neutralizing antibodies that interfere with vaccine administration(s); iv) direct effects of viral vectors on the viability, maturation and antigen-presentation ability of transduced cells (Jenne L. et al., *Trends Immunol.*, 22:102-107, 2001).

TABLE I

Recovery of ADHAPI-Cells and control cells

| Cell Type | ADHAPI-Cells | Control cells |
|---|---|---|
| B-EBV[a] | 114 ± 25 | 175 ± 51 |
| PWM-B[b] | 16 ± 5 | 38 ± 17 |
| CD40L-B[c] | 75 ± 27 | 96 ± 5 |
| PWM-PBMC[d] | 26 ± 11 | 45 ± 16 |
| PHA-PBMC[e] | 23 ± 10 | 63 ± 25 |
| PHA+PWM-PBMC[f] | 35 ± 28 | 63 ± 36 |

[a]Data represent the mean % ±SD of recovered cells as compared to the number of cells (100%) utilized for their generation in 3 (a), 4 (b), 4 (c), 4 (d), 7 (e) and 5 (f) independent experiments.

TABLE II

Phenotypic profile of ADHAPI-Cells compared to autologous control cells*

| | ADHAPI Cells | | | | | |
|---|---|---|---|---|---|---|
| Antigen | CD40L-B[a]† | B-EBV[b] | Pwm-PBMC[c] | PWM-B[d] | PHA-PBMC[e] | PHA + PWM-PBMC[f] |
| HLA Class I | ns[j] | ns | ns | ns | ns | 0.02[g] |
| HLA-A Locus | ns | ns | nt[h] | nt | 0.004 | nt |
| HLA-B Locus | ns | ns | nt | nt | 0.05 | nt |
| HLA-A Alleles | 0.01 | ns | ns | ns | 0.008 | 0.006 |
| HLA-B Alleles | ns | ns | nt | nt | ns | nt |
| CD40 | ns | 0.01 | ns | 0.005 | ns | ns |
| CD54 | 0.03 | 0.01 | ns | ns | 0.003 | ns |
| HLA Class II | ns | ns | ns | 0.03 | ns | 0.05 |
| CD56 | nt | nt | nt | ns | nt | nt |
| CD58 | ns | ns | nt | ns | ns | ns |
| CD59 | nt | nt | ns | ns | nt | 0.04 |
| CD80 | 0.05 | ns | ns | ns | ns | ns |
| CD81 | nt | 0.002 | nt | nt | ns | nt |
| CD86 | 0.008 | nt | ns | ns | nt | ns |

*Data were obtained comparing by Student's paired t-test the mean values of mean fluorescence intensity obtained by flow cytometry in 6 (a), 6 (b), 4 (c), 4 (d), 6 (e), and 2 (f) independent experiments. Statistically significant differences were invariably representative of an up-regulated expression of investigated antigen on ADHAPI-Cells compared to autologous control cells.
[j]not significant;
[g]p value;
[h]not tested;
†ADHAPI-Cells/CD40L-B = 82–100% CD20+; Control CD40L-B cells = 87–99% CD20+.

TABLE III

Enzyme-linked immunosorbent assay (ELISA) evaluation of IFN-γ released by autologous (R) (aMLR) and allogeneic (MLR) PBMC (R) stimulated by ADHAPI-Cells (S) or by control cells (S).*

| | AMLR | | MLR | |
|---|---|---|---|---|
| Cell type | Control cells | ADHAPI-Cells | Control cells | ADHAPI-Cells |
| B-EBV[a] | 1770 ± 919 | 2360 ± 850.5[g] | nt[h] | nt |
| PWM-B[b] | 4330 ± 629 | 5530 ± 8040.06 | 4040 ± 721 | 4950 ± 4760.08 |
| CD40L-B[c] | 330 ± 197 | 429 ± 1530.1 | nt | nt |
| PWM-PBMC[d] | 1500 ± 135 | 1520 ± 1750.6 | nt | nt |
| PHA-pBMC[e] | 140 ± 70 | 956 ± 4360.1 | 267 ± 119 | 1040 ± 5450.07 |
| PHA+PWM+PBMC[f] | 790 ± 236 | 831 ± 2440.09 | 819 ± 184 | 830 ± 1690.7 |

*Data represent the mean values ± SD of IFN-γ (pg/ml) released in two (a), four (b), four (c), four (d), three (e) and four (f) independent experiments. S/R ratios were: 3:1 (a), 1:1 (b), 1:2 (e), 1:1 (d), 1:1 (e), 1:2 (f). IFN-γ release was assayed 24 h (a), six days (b), 24 h (c), six days (d), 24 h (e) and 6 days (f) after the beginning of culture;
[g]p value vs control cells obtained by Student's paired t-test;
[h]not tested.

The invention claimed is:

1. A method for generation of cancer-testis antigen (CTA) presenting cells comprising:
   a) collecting peripheral blood mononuclear cells (PBMC) from a subject,
   b) activating said collected cells with one or more activating agents selected from the group consisting of: pokeweed mitogen (PWM), phytohemagglutinin (PHA)/recombinant human interleukin-2 (rhIL-2), pokeweed mitogen (PMW)/phytohemagglutinin (PHA)/recombinant human interleukin-2 (rhIL-2) and CD40L,
   c) culturing and optionally expanding ex vivo said activated cells, and
   d) treating said cultured and optionally expanded cells with a DNA hypomethylating agent four times every 12 hours, replacing half of the culture medium with fresh medium, and then culturing for an additional 48 hours to provide activated PBMC or activated B-lymphocytes concomitantly expressing multiple CTA of the following different families: MAGE-1, MAGE-2, MAGE-3, MAGE-4, NY-ESO-1, GAGE-1-6 and SSX-2, wherein said DNA hypomethylating agent is 5-aza-2'- deoxycytidine.

2. The method according to claim 1, wherein said subject is a mammal.

3. The method according to claim 2, wherein said subject is a human.

4. The method according to claim 2, wherein said subject is a cancer patient.

5. The method according to claim 1, wherein said CTA presenting cells are Epstein-Barr virus-immortalized B-lymphoblastoid cell lines.

6. A method according to claim 1, wherein said CTA presenting cells are pokeweed mitogen (PWM)-activated B-lymphocytes.

7. A method according to claim 1, wherein said CTA presenting cells are CD40L activated B-lymphocytes.

8. A method according to claim 1, wherein said CTA presenting cells are Phytohemagglutinin (PHA)+recombinant human interleukin-2 (rhIL-2)-activated PBMC.

9. A method according to claim 1, wherein said CTA presenting cells are Phytohemagglutinin (PHA)+recombinant human interleukin-2 (rhIL-2)+pokeweed mitogen (PWM)-activated PBMC.

10. Cancer-testis antigen (CTA) presenting cells obtainable by the method according to claim 1.

11. A composition comprising pooled antigens of CTA presenting cells and/or their cellular components according to claim 10.

12. A method for generation of cancer-testis antigen (CTA) presenting cells comprising:
  a) collecting peripheral blood mononuclear cells (PBMC) from a subject,
  b) activating said collected cells with one or more activating agents selected from the group consisting of: pokeweed mitogen (PWM), phytohemagglutinin (PHA)/recombinant/human interleukin-2 (rhIL-2), pokeweed mitogen (PMW)/phytohemagglutinin (PHA)/recombinant human interleukin-2 (rhIL-2) and CD40L,
  c) culturing and optionally expanding ex vivo said activated cells, and
  d) treating said cultured and optionally expanded cells with a DNA hypomethylating agent four times every 12 hours, replacing half of the culture medium with fresh medium, and then culturing for an additional 48 hours to provide activated PBMC or activated B-lymphocytes concomitantly expressing multiple CTA of the following different families: MAGE, GAGE, SSX, SART-1, BAGE, NY-ESO-1, XAGE-1, TRAG-3 and SAGE, wherein said DNA hypomethylating agent is 5-aza-2'-deoxycytidine.

* * * * *